United States Patent [19]
Khuri-Yakub et al.

[11] Patent Number: 5,077,695
[45] Date of Patent: Dec. 31, 1991

[54] NEAR FIELD SCANNING ACOUSTIC MICROSCOPE AND METHOD

[75] Inventors: Butrus T. Khuri-Yakub, Santa Clara County, Calif.; Paul A. Reinholdtsen, Seattle, Wash.

[73] Assignee: Board of Trustees of the Leland Stanford Junior University, Stanford, Calif.

[21] Appl. No.: 434,236

[22] Filed: Nov. 13, 1989

[51] Int. Cl.$^5$ .............................................. G03B 42/06
[52] U.S. Cl. ........................................ 367/7; 367/138; 73/642
[58] Field of Search ...................... 367/7, 138; 73/642, 73/606; 128/663.01

[56] References Cited
U.S. PATENT DOCUMENTS
4,818,110  4/1989  Davidson ............................ 356/358

*Primary Examiner*—Thomas H. Tarcza
*Assistant Examiner*—Daniel T. Pihulic
*Attorney, Agent, or Firm*—Flehr, Hohbach, Test Albritton & Herbert

[57] ABSTRACT

An acoustic microscope in which acoustic energy is focused onto a membrane which includes an aperture which is a fraction of the size of the focal spot of the acoustic beam at the membrane to form fringing fields on the other side of the membrane. Acoustic energy reflected from the membrane is detected. An object to be examined is placed in cooperative relationship with the fringing fields.

7 Claims, 2 Drawing Sheets

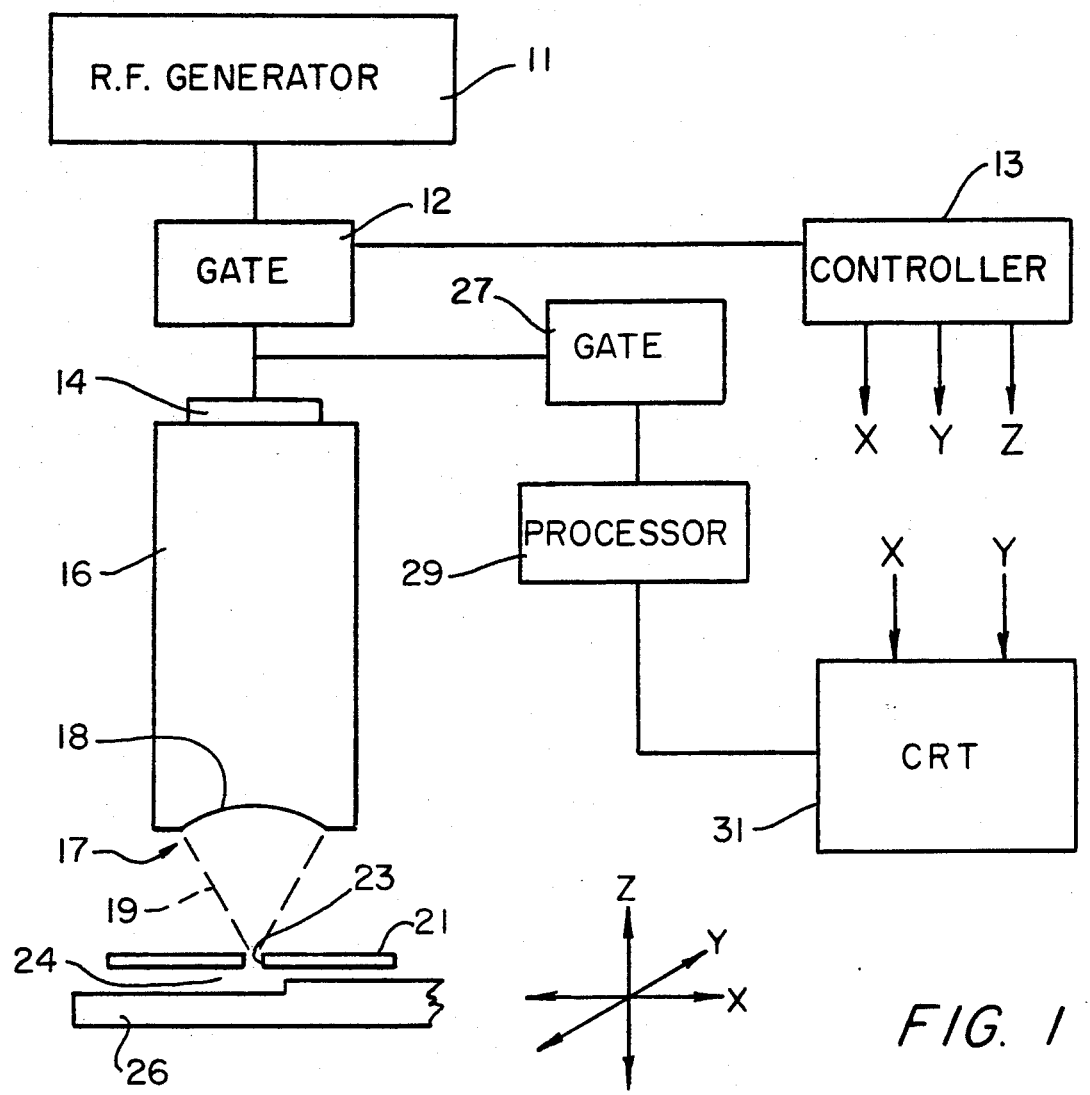
FIG. 1
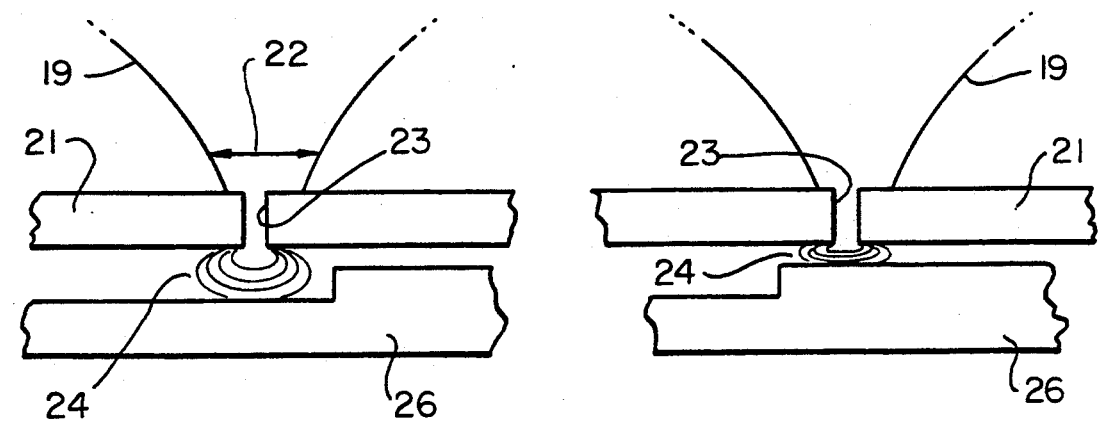
FIG. 2A
FIG. 2B

5,077,695

NEAR FIELD SCANNING ACOUSTIC MICROSCOPE AND METHOD

BRIEF DESCRIPTION OF THE INVENTION

This invention relates to a scanning acoustic microscope and method of imaging, and more particularly to an acoustic microscope and method in which resolution is not limited by the frequency of operation or the physical dimensions of the lens.

DESCRIPTION OF PRIOR ART

Acoustic microscopes are well known. Briefly, prior art acoustic microscopes generate and focus a beam of acoustic energy onto the object being examined. The nature of the object is determined by the amount of perturbation, attenuation or reflection it offers to the acoustic beam in transmission or reflection. The beam of acoustic energy is generated by a piezoelectric element associated with an acoustic lens. Generally, the lens is formed at the end of a rod that receives energy from a piezoelectric element mounted on the end of the rod. The resolution of the acoustic microscope is limited by the size of the spot to which the acoustic energy is focused. The size of the spot is diffraction limited and determined by the wavelength (frequency) of the acoustic wave and by the numerical aperture, F-number, of the lens.

OBJECTS AND SUMMARY OF THE INVENTION

It is a general object of this invention to provide a scanning acoustic microscope in which the resolution is not limited by diffraction BTKY, PR; that is, frequency and numerical aperture of the lens.

It is another object of this invention to provide a scanning acoustic microscope in which the resolution is a fraction of the wavelength of the acoustic energy at the frequency of operation.

It is a further object of this invention to provide an acoustic microscope in which the resolution is determined by the physical dimensions of an aperture.

The foregoing and other objects are achieved by an acoustic microscope in which acoustic energy is focused onto a membrane which includes an aperture which is a fraction of the size of the focal spot of the acoustic beam at the membrane Acoustic energy reflected from the membrane is detected and converted to an electrical signal. An object to be examined is placed on the other side of the membrane and in cooperative relationship with fringing acoustic fields extending from the aperture and moved or scanned through the fringing fields. Variations in the electrical signal are representative of the object surface.

The invention also relates to a method in which acoustic fringing fields are formed at an aperture. An object being examined is moved with respect to the fringing fields. Changes in reflection of an acoustic beam impinging on the aperture are detected to image the surface of the object.

The foregoing objects of the invention will be more clearly understood from the following description, taken in connection with the accompanying drawings.

BRIEF DESCRIPTION OF THE DRAWINGS

FIG. 1 is a schematic diagram illustrating an acoustic scanning microscope incorporating the invention;

FIG. 2A-B are enlarged views of the apertured member and beam spot;

DESCRIPTION OF A PREFERRED EMBODIMENT

Figure 4:
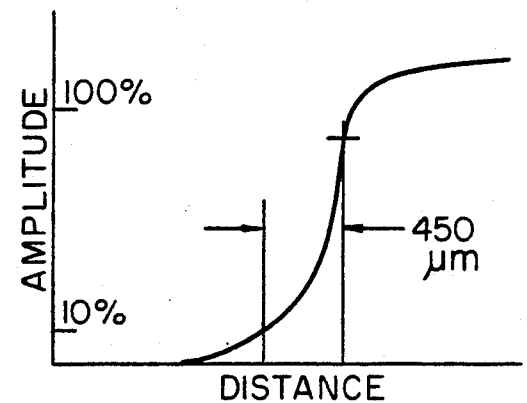
FIG. 4 illustrates the amplitude of the reflected energy as a function of distance for a sharp step traveling through the fringing fields.

Referring now to FIG. 1, the acoustic microscope includes an rf generator 11 which may operate at any frequency up to 1000 MHz BTKY PR. more. The output of the rf generator is applied to a gate 12 controlled by the controller 13.

Referring to FIG. 3A, the gating pulses applied to the gate are shown. The gate is opened and closed periodically to provide pulses of high frequency electrical energy such as shown in FIG. 3C to the piezoelectric transducer 14. The piezoelectric transducer may comprise, for example, a wafer of zinc oxide, lithium niopate, cadmium sulphide, zinc sulphide, or other piezoelectric material. The transducer converts the electrical pulses to sound waves which travel in the rod 16. The rod 16 may be sapphire, quartz or other material which transmits the sound waves to the end 17. The end 17 is shaped with a concave surface to form a lens 18 which focuses the acoustic energy 19 into a beam spot at the surface of a membrane 21. The size 22 (FIG. 2A) of the beam spot is determined by the wavelength of the energy (frequency) and the numerical aperture, the F-number, of the lens 18.

The membrane 21 includes an aperture or pinhole 23 which is a fraction of the size of the beam spot. The pinhole 23 is placed at the focal spot of the acoustic beam and its function is to allow energy to pass through the pinhole. Because the pinhole is smaller than the wavelength of the energy, no propagation mode is allowed. Thus, an insignificant amount of energy is transmitted through the aperture Evanescent waves form a fringing field 24 (FIGS. 2A, 2B). The evanescent field will be confined within a depth corresponding to the pinhole size. The reflected acoustic energy is shown in FIG. 2D. The membrane is made from a material chosen either to have a high impedance to reduce coupling from the region around the pinhole or lossy enough to reduce the coupling from the region around the pinhole. In order to detect the presence of an object 26, it is important to bring the object within the fringing field such as shown in FIG. 2B. When the object 26 is brought within the fringing field, the amplitude of the reflected acoustic energy, FIG. 3D, is changed (FIG. 3E).

Figure 3:
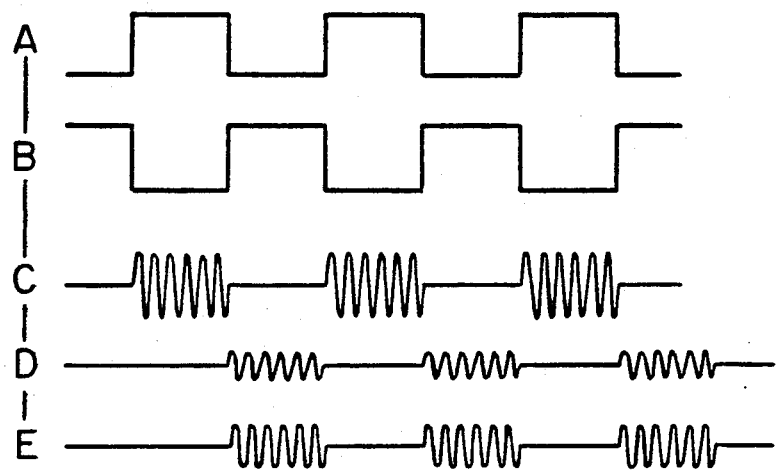
FIGS. 3A-E are waveforms showing the signals at various points in the circuit of FIG. 1.

Referring to FIGS. 1 and 3, after gate 12 is turned on by the gating pulses, FIG. 3A, gate 27 is turned on by the sampling pulses, FIG. 3B, which open the gate 27 and pass the reflected waves (FIGS. 3D and 3E) to a processor 29. The processor measures the amplitude of the received waves and applies the amplitude signal to the intensity input of a CRT 31 or to a signal recorder. When the object is outside the fringing field, the reflected energy has a relatively low amplitude, whereas when the object is within the fringing fields, the reflected energy has a different amplitude. The piezoelectric transducer 12 converts the energy to an electrical signal which is processed to form the amplitude signal.

Referring to FIG. 4, the output as a function of position of an edge is shown as the object 26 passes through the fringing field. The front edge of the step strikes the field, the amplitude of the outputs begins to increase and increases rapidly until the object is within the complete fringing field.

The object is moved in the z direction by a suitable mechanical means, such as a micrometer or the like, to bring the object within the fringing field. The object is then scanned in the x and y direction by a suitable scanner. The scanner may include motors, hydraulic actuators, or the like and position transducers. Output position signals from the drives are applied to the x and y electrodes of the CRT whereby the CRT will display a pattern of the surface of the object being scanned.

In an acoustic microscope operating at a frequency of 3 MHz BTKY PR and with a transducer having an F-number of 0.7, the wavelength of the acoustic wave in water in which the object was immersed was 500 $\mu$m. Using a brass shim or membrane 125 $\mu$m thick and with a 125 $\mu$m in diameter pinhole, the sharp edge of a ceramic sample was imaged. The ceramic sample was brought within 50 $\mu$m from the shim and scanned across the pinhole. Two scans were made; one with and one without the shim. The 10% to 90% rise of the edge of the signal indicating the presence of ceramic was reduced from 450 $\mu$m to 160 $\mu$m in one measure. This result indicates that indeed it is possible to make a near-field scanning microscope and obtain resolution that is sub-wavelength, 160 $\mu$m.

Figure 5:
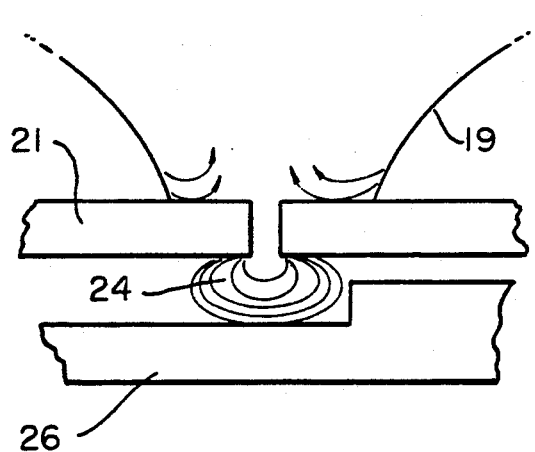
FIG. 5 shows an acoustic scanning microscope in accordance with the invention in which the apertured membrane is placed off focus.

We have found that if the membrane 21 is defocused with respect to the focal spot of the acoustic beam, the image contrast may be enhanced. This is illustrated in FIG. 5 where there is mode conversion at the membrane.

Figure 6:
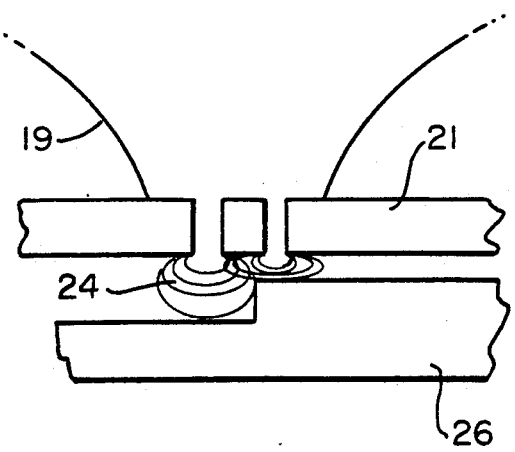
FIG. 6 shows an acoustic microscope in accordance with the invention in which the apertured member includes spaced apertures to provide differential information.

FIG. 6 shows a membrane with two pinholes or apertures. Differential signals are generated to provide signals indicative of variations in the surface of the object being scanned.

Thus, it is seen that there has been provided a scanning acoustic microscope in which the resolution is determined by the size of a pinhole or aperture and not by the wavelength of the acoustic energy or the numerical aperture of the lens.

We claim:

1. The method of acoustically imaging an object which comprises
    generating an acoustic beam at a predetermined frequency,
    focusing the acoustic beam at a predetermined focal point to form a focal spot located adjacent the object to be imaged,
    placing a membrane including a pinhole smaller than the focal spot in the acoustic beam to receive the beam on one side of said membrane whereby to form fringing fields at the other side of same membrane,
    bringing the object into the fringing field,
    detecting acoustic energy reflected from the membrane as the object is moved in the fringing field, and
    converting the detected energy to an electrical signal.

2. The method as in claim 1 in which the membrane is positioned so that the pinhole is at the focus of the acoustic beam.

3. The method as in claim 1 in which the membrane is positioned so that the pinhole is displaced from the focal spot.

4. A scanning acoustic microscope of the type including
    a transducer and a lens for forming and focusing an acoustic beam of predetermined frequency to define a focal spot of a size determined by said lens and frequency comprising
    a membrane including an aperture having a smaller size than said focal spot, said membrane positioned in said beam to receive and reflect acoustic energy from one surface and forming a fringing field at the aperture on the other surface of the membrane,
    means for positioning an object to be examined adjacent said membrane and in cooperation with the fringing field,
    means for moving the object in the fringing fields, and
    means for detecting the reflected energy and forming an output signal representative of the amplitude of the reflected energy.

5. A scanning microscope as in claim 4 in which said membrane is positioned at the focal spot of said acoustic beam.

6. A scanning microscope as in claim 4 in which said membrane is positioned so that the aperture is displaced from the focal spot.

7. A scanning microscope of the type including a transducer and a lens for forming and focusing an acoustic beam to a focal spot comprising
    a member including at least one aperture having a size smaller than the focal spot,
    means for positioning said member so that said at least one aperture is in said acoustic beam whereby fringing fields are formed at said aperture, and
    means for positioning an object to be examined adjacent said membrane for cooperation with the fringing fields.

* * * * *